US008974376B2

(12) United States Patent
Okamoto

(10) Patent No.: US 8,974,376 B2
(45) Date of Patent: Mar. 10, 2015

(54) INTRODUCING DEVICE SYSTEM WITH BENDING CONTROL

(71) Applicant: Olympus Medical Systems Corp., Tokyo (JP)

(72) Inventor: Yasuhiro Okamoto, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/167,530

(22) Filed: Jan. 29, 2014

(65) Prior Publication Data

US 2014/0190305 A1   Jul. 10, 2014

Related U.S. Application Data

(63) Continuation of application No. PCT/JP2013/065825, filed on Jun. 7, 2013.

(30) Foreign Application Priority Data

Jul. 9, 2012   (JP) ................................. 2012-153865

(51) Int. Cl.
*A61B 1/005*   (2006.01)
*B25J 18/06*   (2006.01)
(Continued)

(52) U.S. Cl.
CPC .............. *B25J 18/06* (2013.01); *A61B 1/0057* (2013.01); *A61B 1/0051* (2013.01); *G02B 23/2476* (2013.01); *A61B 1/00133* (2013.01); *A61B 1/0052* (2013.01); *Y10S 901/21* (2013.01)
USPC ............................. 600/152; 600/146; 901/21

(58) Field of Classification Search
CPC ....... A61B 1/0051; A61B 1/0057; B25J 18/06
USPC .......................................... 600/146, 152, 118
See application file for complete search history.

(56) References Cited

U.S. PATENT DOCUMENTS 8,382,659 B2 *   2/2013   Ashida et al. ................. 600/146
8,708,892 B2 *   4/2014   Sugiyama et al. ............ 600/117
2002/0026096 A1   2/2002   Motoki et al.
(Continued)

FOREIGN PATENT DOCUMENTS

EP   1 787 572 A1   5/2007
JP   06-105799 A   4/1994
(Continued)

*Primary Examiner* — John P Leubecker
(74) *Attorney, Agent, or Firm* — Scully, Scott, Murphy & Presser, P.C.

(57) ABSTRACT

An introducing device system includes: an insertion portion; a bending portion which is provided at the insertion portion; an operation portion through which an input operation is performed for bending the bending portion; a pulling member connected to the bending portion and pulled in accordance with the operation through the operation portion; a detection section that detects a moving state of the pulling member; a driving unit that rotationally drives; a driving force transmitting unit including an inner circumferential surface configured to be able to contact an outer circumferential surface of the driving unit, and an outer circumference on which the pulling member is wound, the driving force transmitting unit being reduced in diameter in accordance with pulling of the pulling member; and a driving unit control section controls the driving unit when the moving state detected by the detection section is different from a state determined in advance.

5 Claims, 8 Drawing Sheets

(51) Int. Cl.
*G02B 23/24* (2006.01)
*A61B 1/00* (2006.01)

(56) References Cited

U.S. PATENT DOCUMENTS

| | | | |
|---|---|---|---|
| 2003/0092965 A1* | 5/2003 | Konomura et al. | 600/146 |
| 2003/0195389 A1 | 10/2003 | Motoki et al. | |
| 2006/0178563 A1* | 8/2006 | Hirata et al. | 600/152 |
| 2007/0112255 A1* | 5/2007 | Ikeda et al. | 600/146 |
| 2007/0150155 A1 | 6/2007 | Kawai et al. | |
| 2009/0076330 A1* | 3/2009 | Ashida | 600/146 |
| 2011/0065994 A1* | 3/2011 | Kudoh et al. | 600/146 |
| 2013/0267775 A1* | 10/2013 | Okamoto | 600/109 |

FOREIGN PATENT DOCUMENTS

| | | | |
|---|---|---|---|
| JP | 2001-286437 A | 10/2001 |
| JP | 2003-325437 A | 11/2003 |
| JP | 2006-055349 A | 3/2006 |
| JP | 2009-226125 A | 10/2009 |
| JP | 2011-098078 A | 5/2011 |
| WO | WO 2006/019136 A1 | 2/2006 |

* cited by examiner

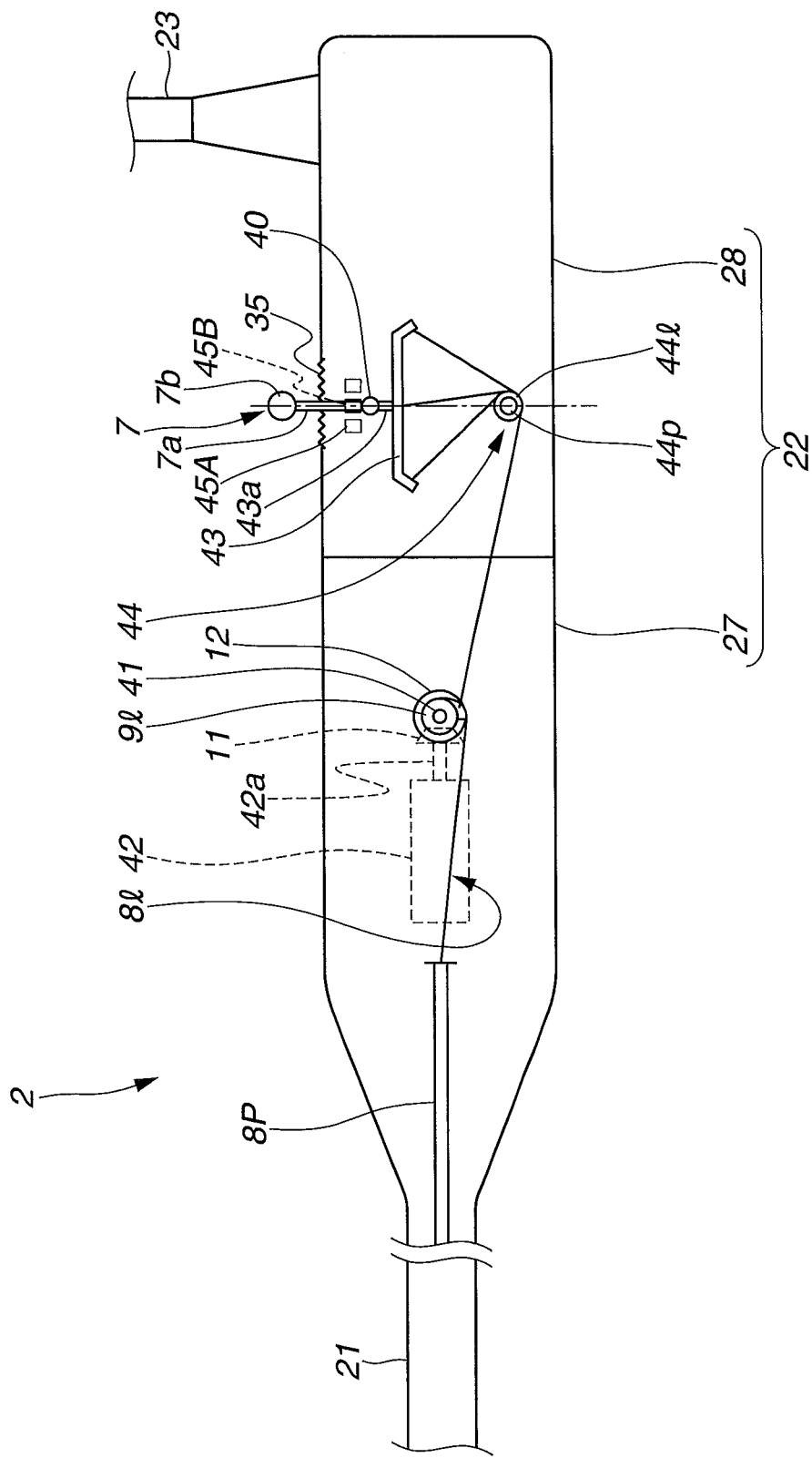

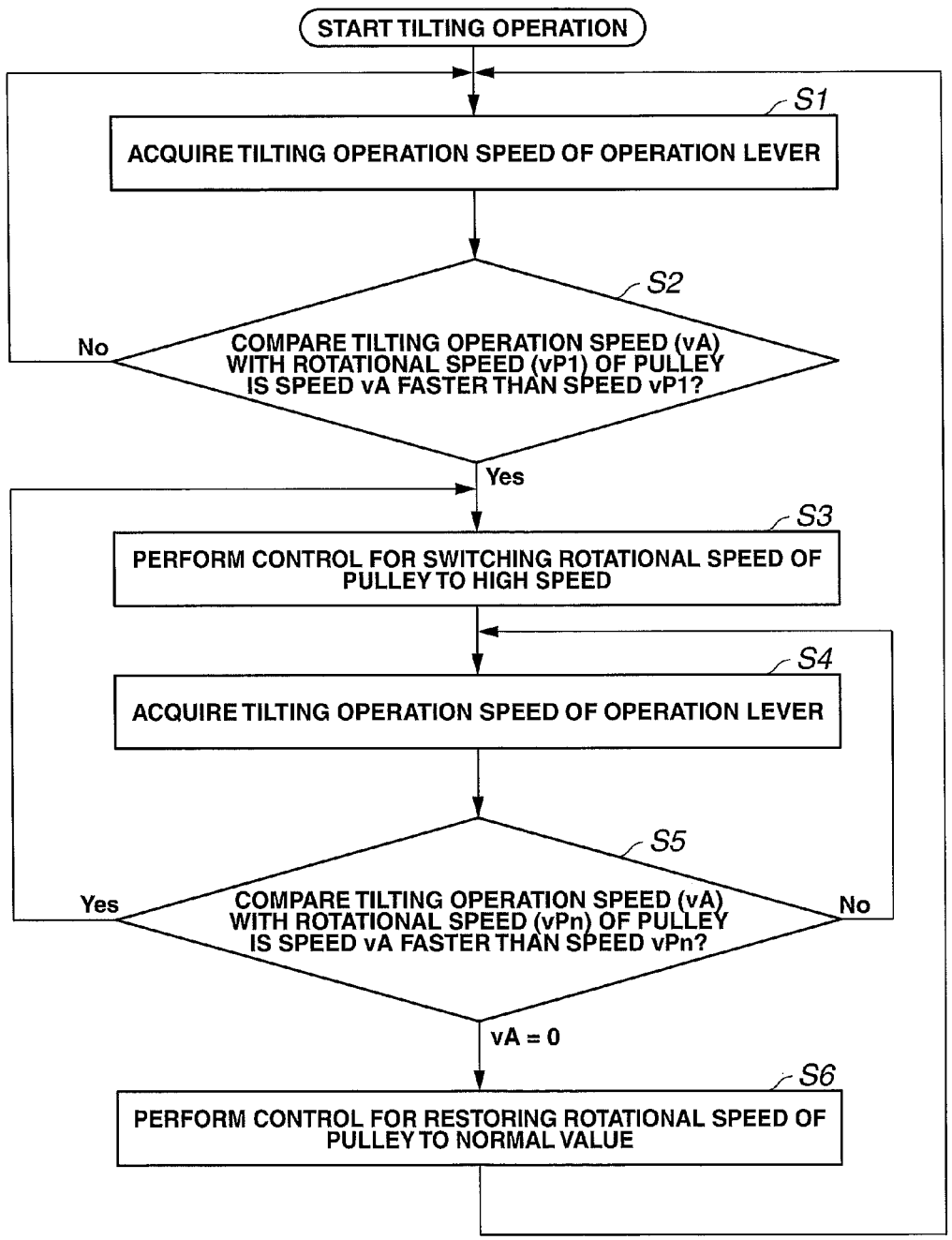

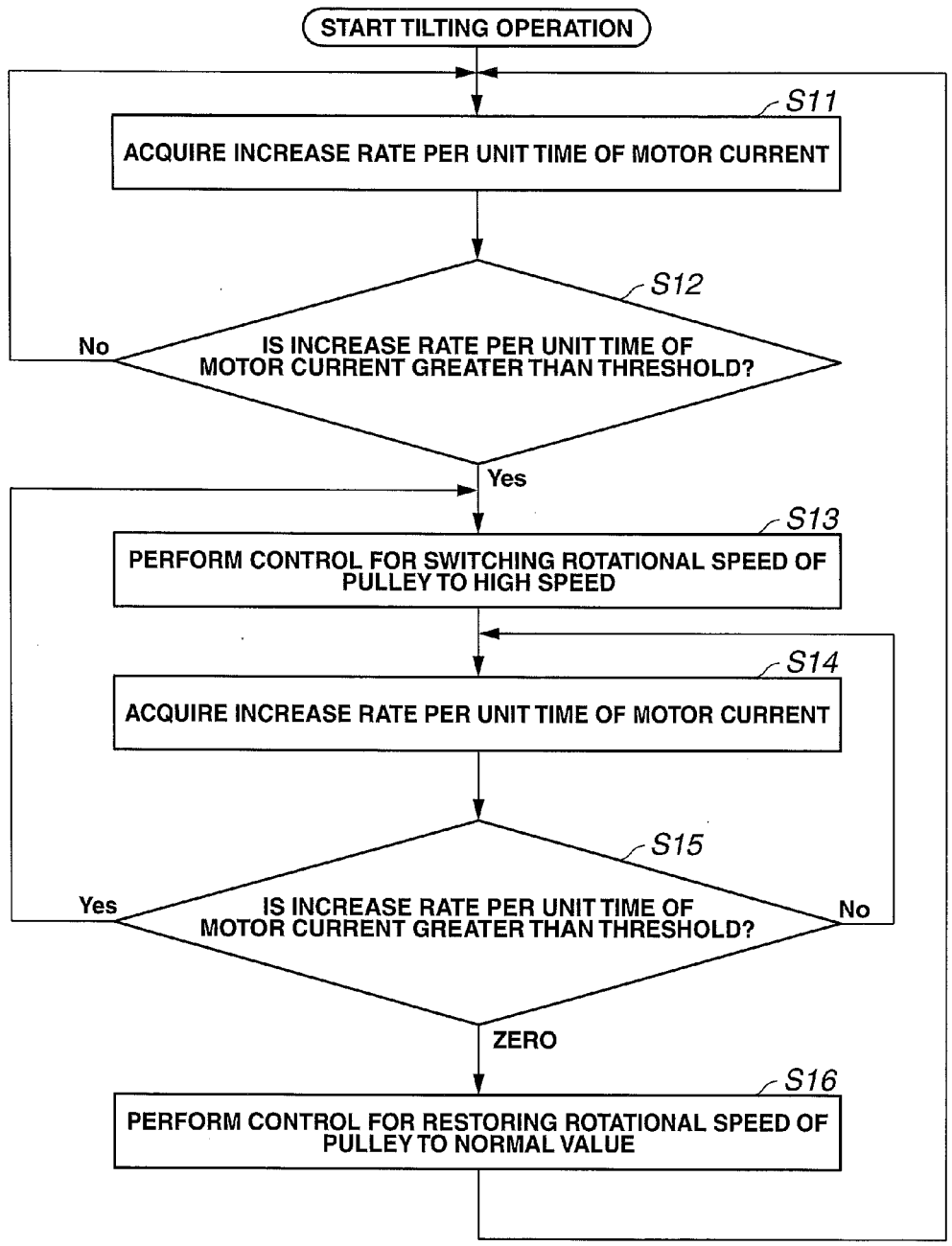

_US 8,974,376 B2_

INTRODUCING DEVICE SYSTEM WITH BENDING CONTROL

CROSS REFERENCE TO RELATED APPLICATION

This application is a continuation application of PCT/JP2013/065825 filed on Jun. 7, 2013 and claims benefit of Japanese Application No. 2012-153865 filed in Japan on Jul. 9, 2012, the entire contents of which are incorporated herein by this reference.

BACKGROUND OF THE INVENTION

1. Field of the Invention

The present invention relates to an introducing device system which reduces an amount of operation force for operating a bending operation device configured to pull a pulling member that causes a bending portion to bend.

2. Description of the Related Art

Endoscopes, for example, as introducing devices for introducing an insertion portion into a subject, are used in medical fields, industrial fields, and the like. In the case of the endoscopes in medical fields, observation, etc., are performed by inserting an insertion portion into a body. On the other hand, in the case of the endoscopes in industrial fields, observation, etc., are performed by inserting an insertion portion into a piping or into a construction such as an engine.

An endoscope generally includes an observation optical system at a distal end portion of an insertion portion. Furthermore, such an endoscope includes a bending portion that bends in up, down, left and right directions, for example, on the distal end side of the insertion portion. In addition, the endoscope includes, at the proximal end of the insertion portion, an operation portion including a bending operation device for causing the bending portion to bend.

A bending knob which is rotationally moved, an operation lever which is tilted, etc., are publicly known as the bending operation device. Such a bending operation device and, for example, a distal end bending piece constituting a bending portion are coupled to each other with wires as pulling members. In the endoscope thus configured, the bending portion is bent by an operator rotating or tilting the bending operation device with his or her fingers, to directly pull or relax the wires.

Japanese Patent Application Laid-Open Publication No. 2003-325437 discloses the endoscope including an electric assist mechanism. The endoscope is provided with an operation instruction lever (corresponding to an operation lever 7 of the present invention), for example, as a bending operation device. The bending portion of the endoscope is bent by the bending instruction lever being tilted to bring an operation wire corresponding to the tilting operation, which is fixed to an arm member, into contact with a pulley rotated with a motor, to move the wire in the rotational direction of the pulley.

The endoscope disclosed in the above-described Japanese Patent Application Laid-Open Publication No. 2003-325437 reduces the amount of the operation force required for the operator to operate the bending operation device by using the rotational force transmitted from the pulley to the operation wire when the operation wire contacts the pulley rotated with the motor as an amount of force for moving the operation wire.

In addition, in the endoscope disclosed in the Japanese Patent Application Laid-Open Publication No. 2003-325437, when the distal end portion of the insertion portion contacts, for example, a wall or the like, during the bending operation, the operational feeling felt by the operator who operates the bending operation device changes to enable the user to feel that the distal end portion contacts somewhere.

Japanese Patent Application Laid-Open Publication No. 2011-098078 discloses the endoscope apparatus which enables an operation input performed at the main body portion to be accurately reflected in the scope unit. In the endoscope apparatus, repetition of the loop from the step S101 to the step S105 shown in FIG. 8 in the Japanese Patent Application Laid-Open Publication No. 2011-098078 causes the motor 61 of the bending driving unit 160 to rotate in conjunction with the position toward which the user tilts the J/S 41, to thereby cause the bending portion 113 to bend, or repetition of the loop from the step S201 to the step S204 causes the motor 61A of the bending driving unit 260 to rotate in conjunction with the position toward which the user tilts the J/S 41, to thereby cause the bending portion 213 to bend.

The endoscope apparatus generates a driving signal for operating the bending driving unit so as to control the bending speed of the bending portion of the scope unit based on information on the acceleration when the J/S is tilted, to rotate the motor and bend the bending portion.

SUMMARY OF THE INVENTION

An introducing device system according to one aspect of the present invention includes: an insertion portion configured to be inserted into a subject; a bending portion which is provided at the insertion portion and configured to be bendable; an operation portion through which an input operation is performed for bending the bending portion; a pulling member connected to the bending portion and pulled in accordance with the input operation through the operation portion; a detection section configured to detect a moving state of the pulling member that moves in accordance with the input operation; a driving unit that rotationally drives; a driving force transmitting unit including an inner circumferential surface configured to be able to contact an outer circumferential surface of the driving unit, and an outer circumference on which the pulling member is wound, the driving force transmitting unit being reduced in diameter in accordance with pulling of the pulling member; and a driving unit control section configured to perform control for increasing a rotational speed of the driving unit when the moving state detected by the detection section is different from a state determined in advance.

BRIEF DESCRIPTION OF THE DRAWINGS

FIGS. 1 to 5 relate to a first embodiment of the present invention, and FIG. 1 illustrates an endoscope system including an endoscope as an introducing device.

FIG. 2 illustrates the endoscope.

FIG. 3 illustrates a configuration of an operation portion of the endoscope.

FIG. 5 is a flowchart for describing a control by a control device.

FIGS. 6 to 8 relate to a second embodiment of the present invention, and FIG. 6 illustrates an endoscope system including an endoscope as an introducing device.

FIG. 8 is a flowchart for describing a control by a control device.

DETAILED DESCRIPTION OF THE PREFERRED EMBODIMENTS

Hereinafter, embodiments of the present invention will be described with reference to drawings.

In the embodiments to be described below, an introducing device will be described by taking an endoscope as an example.

Description will be made on a first embodiment of the present invention with reference to FIGS. 1 to 5.

Figure 1:
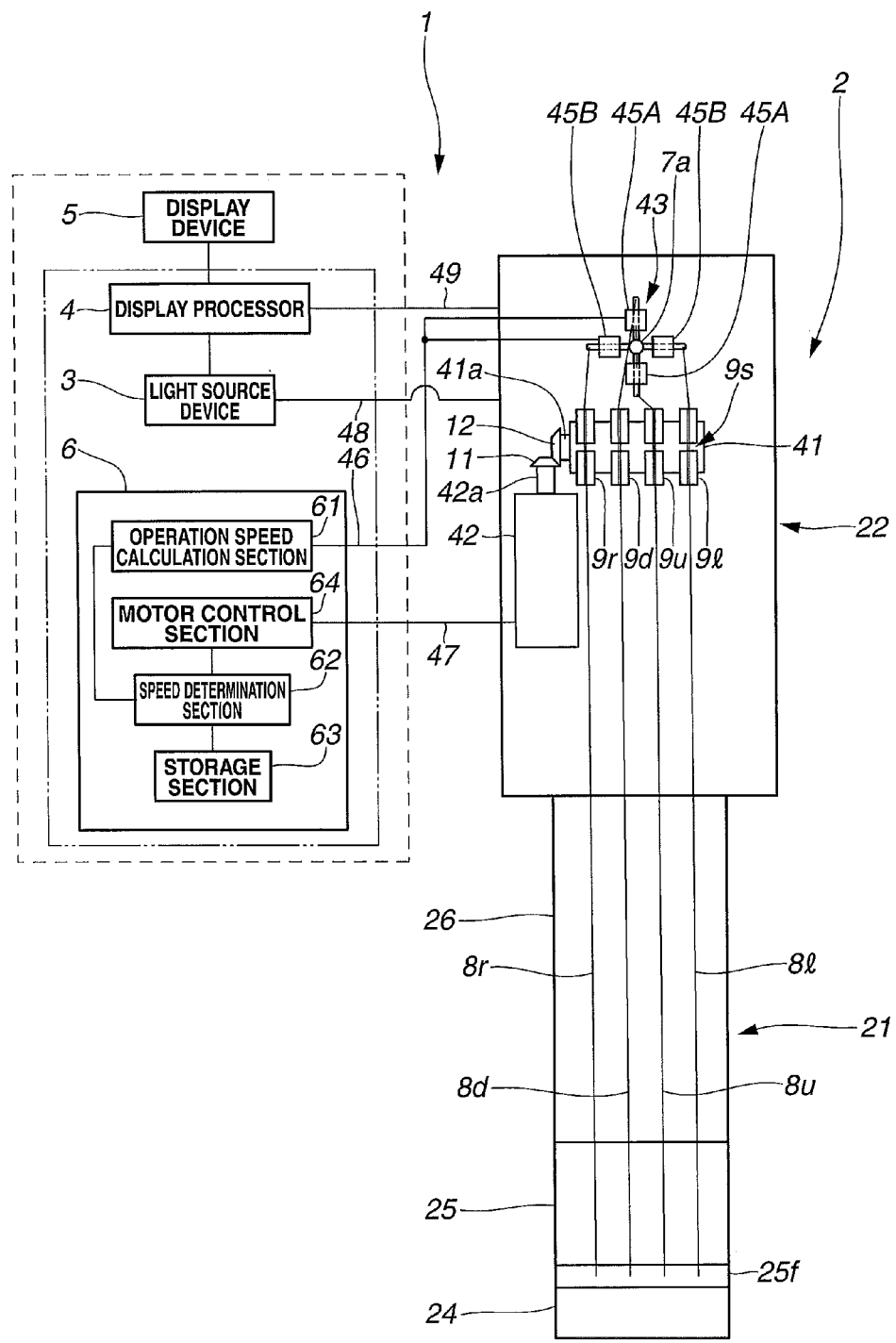

As shown in FIG. 1, an endoscope system 1 according to the present embodiment mainly includes an endoscope 2, a light source device 3, a display processor 4, a display device 5, and a control device 6.

The light source device 3 generates illumination light for endoscope. The display processor 4 is an image processing apparatus that performs various kinds of image processing on image data obtained by image pickup with an image pickup section. The display device 5 receives a video signal outputted from the display processor 4 to display an observed image.

FIG. 1 shows the light source device 3, the display processor 4, and the control device 6 as separated bodies. However, the light source device 3, the display processor 4, and the control device 6 may be integrally configured as shown by the two-dot chain line. Alternatively, the light source device 3, the display processor 4, the display device 5, and the control device 6 may be integrally configured as shown by the dashed line.

Figure 2:
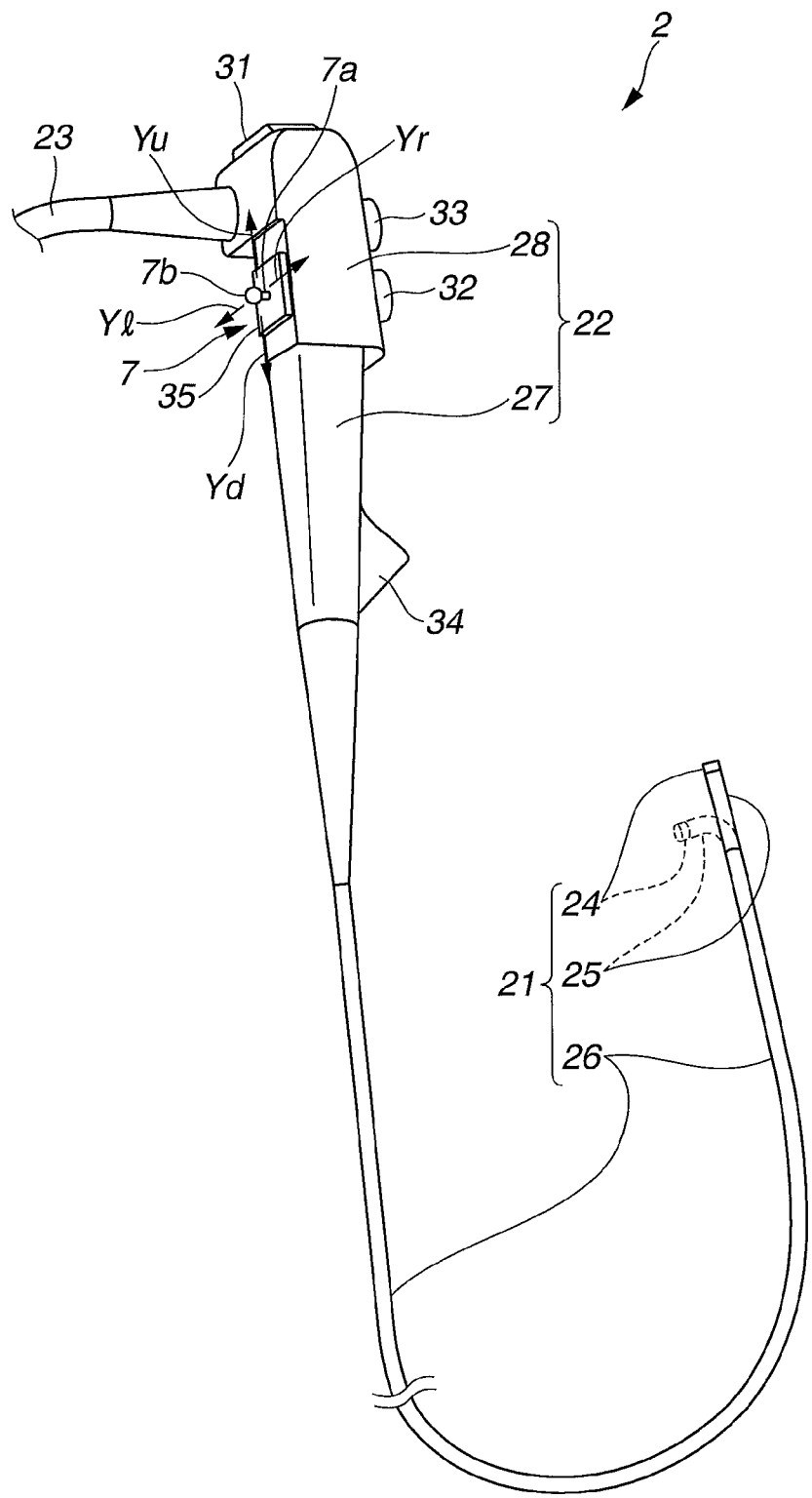

As shown in FIGS. 1 and 2, the endoscope 2 according to the present embodiment mainly includes an elongated insertion portion 21, an operation portion 22 provided on a proximal end of the insertion portion 21 in a linked manner, and a universal cord 23 extending from a side portion of the operation portion 22.

The insertion portion 21 includes in a linked manner in the following order from the distal end side: a distal end portion 24, a bending portion 25 configured to be bendable in up, down, left and right directions, for example, and a flexible tube portion 26 which is long and has flexibility. The distal end portion 24 incorporates an image pickup section (not shown) including an image pickup device.

The operation portion 22 as shown in FIGS. 2 and 3 is an operation input unit and includes a grasping portion 27 provided so as to link to the insertion portion 21, and an operation portion main body 28 provided so as to link to the grasping portion 27. In the part on the distal end side of the operation portion main body 28 where a largest vacant space is present, an operation lever 7, etc., which constitute a bending operation device for performing input operation for causing the bending portion 25 to bend are provided.

The operation lever 7 is provided from an opening (not shown) formed on one surface of the operation portion main body 28 so as to be substantially perpendicular to the longitudinal axis of the operation portion 22.

The bending portion 25 is configured to bend in an up direction, a right direction, a down direction, a left direction, a direction between the up direction and the right direction, etc., by pulling and relaxing operation wires (hereinafter, referred to as wires) which are pulling members to be described later. Tilting operation including the tilting direction and tilting angle of the operation lever 7, as shown by the arrows Yu, Yd, Yl, and Yr in FIG. 2, causes wires corresponding to the tilting operation to be pulled or relaxed.

The bending portion 25 is configured to bend in four directions, i.e., the up, down, left, and right directions in the present embodiment. The bending portion 25, however, may be configured to bend in two directions, i.e., the up and down directions. The reference signs u, d, l, and r indicate the up direction, the down direction, the left direction, and the right direction, which are bending directions of the bending portion 25, respectively.

In the description below, the reference sign 8u indicates an upper wire, and the reference sign 9d indicates a lower C-shaped ring, for example. The lower-case character "l" is shown with the cursive script in the drawings, to discriminate from the numeric character "1".

The operation portion main body 28 includes, at predetermined positions on the exterior thereof, a switch 31 for giving instructions for various image pickup operations of the image pickup apparatus (not shown) provided in the distal end portion 24, an air/water feeding button 32, and a suction button 33, for example, in addition to the operation lever 7. The grasping portion 27 includes, on the exterior thereof, a channel insertion port 34 which communicates with a treatment instrument channel (not shown). The reference sign 35 indicates a cover member which watertightly covers an operation lever projection port and closely contacts a shaft portion 7a, to hold the operation lever 7 so as to allow the tilting operation of the operation lever.

A signal cable connected to the image pickup apparatus, an electric wire that supplies power to a motor to be described later (see the reference sign 42 in FIGS. 1 and 3), a light guide fiber bundle that transmits illumination light of the light source device 3, an air feeding tube, a water feeding tube, a suction tube, and the like are inserted through the universal cord 23, though illustration of these components is omitted.

As shown in FIGS. 1 and 3, the operation portion 22 mainly includes inside thereof a pulley 41, a motor 42, a suspender frame 43, a group of guide rollers 44, rotation detection sensors 45A and 45B which constitute a detection section, four wires 8u, 8d, 8l, and 8r, and four C-shaped rings 9u, 9d, 9l, and 9r.

The four wires 8u, 8d, 8l and 8r are pulling members. The distal end parts of the wires 8u, 8d, 8l, and 8r are each fixedly attached to a distal end piece 25f which constitutes the bending portion 25. The middle parts of the wires 8u, 8d, 8l, and 8r are wound respectively on the outer circumferential surfaces, which are winding portions, of the four C-shaped rings 9u, 9d, 9l, and 9r. The proximal end parts of the wires 8u, 8d, 8l, and 8r are respectively coupled to four wire mounting portions provided to the suspender frame 43. The four wires 8u, 8d, 8l, and 8r include a pair of upper and lower wires 8u, 8d for up/down bending, and a pair of left and right wires 8l, 8r for left/right bending.

The four C-shaped rings 9u, 9d, 9l, and 9r are driving force transmitting units made of resin. Each of the four C-shaped rings 9u, 9d, 9l, and 9r is formed in a substantially C-shape with a slit 9s and configured to be contractable and expandable. The four C-shaped rings 9u, 9d, 9l, and 9r are arranged on the outer circumferential surface of the elongated pulley 41 in a loosely-fitted manner.

In other words, a predetermined gap is formed between the inner circumferential surfaces of the four C-shaped rings 9u, 9d, 9l, and 9r and the outer circumferential surface of the pulley 41. Each of the slits 9s is a diameter-changing portion.

The motor 42 causes the pulley 41 to rotate. The pulley 41 and the motor 42 constitute a driving unit. The driving unit generates a driving force for driving to bend the bending portion 25 by rotational driving.

The suspender frame 43 has a substantially cross shape, and the end portions of the cross shape are respectively provided with wire mounting portions to which the proximal end portions of the wires 8u, 8d, 8l, and 8r are coupled. The suspender frame 43 includes at the center portion thereof a frame projection portion 43a which is a central axis portion of the frame 43. The shaft portion 7a of the operation lever 7 and the frame projection portion 43a are coaxially mounted and fixed through a universal joint 40. The operation lever 7 and the suspender frame 43 serve as the bending operation device. Input operation is performed through the bending operation device when a user pulls a desired wire among the wires 8u, 8d, 8l, and 8r. The reference sign 7b indicates a finger contact portion that is integrally fixed to the distal end of the shaft portion 7a.

As shown in FIG. 3, the group of guide rollers 44 is a wire running path changing member. The group of guide rollers 44 is configured such that a plurality of guide rollers 44u, 44d, 44l, and 44r are rotatably arranged on a roller shaft 44p. The group of guide rollers 44 changes the running paths of the four wires 8u, 8d, 8l, and 8r in the operation portion 22.

The reference sign 8P indicates a coil pipe. The coil pipe 8P is made of metal, for example, and has a through hole through which one wire can be advanceably/retractably inserted. The coil pipe 8P is provided corresponding to each of the wires 8u, 8d, 8l, and 8d.

As shown in FIG. 1, the rotation detection sensors 45A and 45B detect the tilting action of the shaft portion 7a, which is a bending operation amount, when the operation lever 7 is tilted, to output the detection value obtained by the detection to the control device 6. The rotation detection sensors 45A, 45B include, for example, a pair of up/down rotation detection sensors 45A that detect the moving amount and the time at the time of up/down bending operation, and a pair of left/right rotation detection sensors 45B that detect the moving amount and the time at the time of left/right bending operation.

The reference signs 46, 47, 48, and 49 represent a signal cable, a control cable, an illumination cable, and an image pickup cable, respectively.

The control device 6 is a control unit and includes an operation speed calculation section 61, a speed determination section 62, a storage section 63, and a motor control section 64.

The operation speed calculation section 61 is a detection section and calculates a tilting operation speed (v) of the operation lever 7 based on the moving distance as the tilted amount and the elapsed time, which are the detection values outputted from the rotation detection sensors 45A and 45B, to output the calculated tilting operation speed to the speed determination section 62.

The speed determination section 62 compares the tilting operation speed (v) of the operation lever 7 outputted from the operation speed calculation section 61 to the speed determination section 62 with the rotational speed (V) of the pulley 41 registered in the storage section 63. The speed determination section 62 outputs a notifying signal to the motor control section 64 when the tilting operation speed (v) is faster than the rotational speed (V).

The motor control section 64 is a driving unit control section and controls the rotational speed of the pulley 41 by controlling the rotational speed of the motor 42. The motor control section 64 outputs a control signal to the motor 42 when receiving the notifying signal from the speed determination section 62, to set the rotational speed of the pulley 41 at a speed faster than the tilting operation speed by a predetermined speed.

The rotational driving force of the motor 42 according to the present embodiment is transmitted to the pulley 41 through a first bevel gear 11 provided to the motor shaft 42a and a second bevel gear 12 provided to the shaft portion 41a of the pulley 41.

In the endoscope 2 according to the present embodiment, when the operator performs input operation for tilting the operation lever 7, for example, in the direction of the arrow Yu in FIG. 2, the upper wire 8u is pulled to cause the bending portion 25 to bend in the up direction. Since the upper wire 8u is wound on the upper C-shaped ring 9u, the upper C-shaped ring 9u is gradually reduced in diameter in accordance with the pulling of the upper wire 8u. As a result, the gap between the upper C-shaped ring 9u and the outer circumferential surface of the pulley 41 is gradually reduced.

The tilting operation of the operation lever 7 causes the upper wire 8u to be pulled further, which brings the inner circumferential surface of the upper C-shaped ring 9u into contact with the outer circumferential surface of the pulley 41, and then the inner circumferential surface of the upper C-shaped ring 9u presses the outer circumferential surface of the pulley 41. As a result, the resistance force between the inner circumferential surface of the upper C-shaped ring 9u and the outer circumferential surface of the pulley 41 gradually increases.

When the resistance force reaches a desired value during the tilting operation, the inner circumferential surface of the upper C-shaped ring 9u as the transmitting section and the outer circumferential surface of the pulley 41 are brought into, what is called, an engaged state, and the rotational force of the pulley 41 is transmitted to the upper C-shaped ring 9u. Then, the upper C-shaped ring 9u independently rotates in accordance with the rotation of the pulley 41, thereby causing the upper wire 8u wound on the upper C-shaped ring 9u to be moved in the rotation direction of the upper C-shaped ring 9u, i.e., the pulling direction. The upper wire 8u is thus pulled with the amount of force applied by the operator to perform tilting operation of the operation lever 7 and the rotational force of the upper C-shaped ring 9u to which the rotational force of the pulley 41 is transmitted, which reduces the amount of force required for the operator to perform tilting operation of the operation lever 7.

In the present embodiment, when the operator tilts the operation lever 7 in the direction of the arrow Yd, in the direction of the arrow 1, in the direction of the arrow r, in the direction between the arrow u and the arrow r, the amount of force required for the operator to perform tilting operation of the operation lever 7 is reduced similarly as described above.

When the middle parts of the wires 8u, 8d, 8l, and 8r wound on the C-shaped rings 9u, 9d, 9l, and 9r become a relaxed state, the C-shaped rings 9u, 9d, 9l, and 9r are brought into a loosely fitted state with respect to the outer circumferential surface of the pulley 41, which releases the above-described engaged state.

Now, the working of the above-described endoscope system 1 will be described with reference to FIG. 4A to FIG. 5.

Figure 4A:
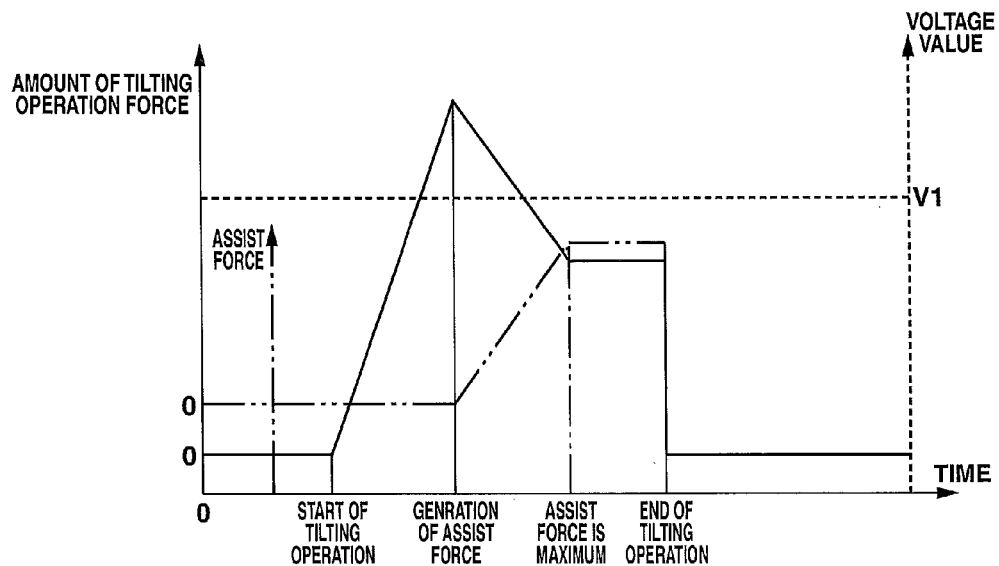
FIG. 4A illustrates a relationship among an amount of a tilting operation force, an assist force, and a voltage value from the start of the tilting operation until the end of the tilting operation in the case where the tilting operation speed is slower than the rotational speed of the pulley.
Figure 4B:
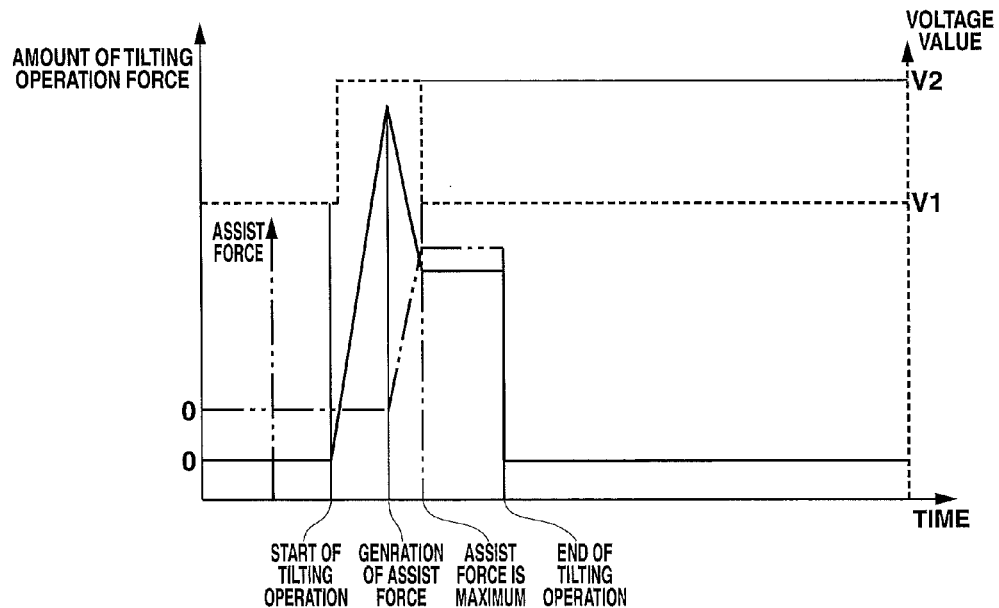
FIG. 4B illustrates a relationship among the amount of the tilting operation force, the assist force, and the voltage value from the start of the tilting operation until the end of the tilting operation.

In the above-described endoscope system 1, the motor 42 included in the endoscope 2 is driven at a voltage V1 determined in advance, with the start of the examination, as shown in the dashed lines in FIG. 4A and FIG. 4B. In this initial state, the pulley 41 is rotated at the rotational speed (vP1) in the direction in which the wires 8u, 8d, 8l, and 8r are pulled.

In the endoscope 2, when the shaft portion 7a of the operation lever 7 is in the upright state, the wires 8u, 8d, 8l, and 8r wound on the C-shaped rings 9u, 9d, 9l, and 9r arranged on the pulley 41 are all in a predetermined relaxed state. In other words, all the C-shaped rings 9u, 9d, 9l, and 9r are in a sliding state with respect to the pulley 41, which maintains the bending portion 25 in the linear state.

When the operator tilts the operation lever 7 in the direction of the arrow Yu in FIG. 1 in order to cause the bending portion 25 to bend in the up direction, for example, the tilting operation shown in FIGS. 4A and 4B is started. The control device 6 starts the control shown in the flowchart in FIG. 5 in accordance with the start of the tilting operation.

That is, at the same time as the tilting operation of the operation lever 7, the tilting operation speed starts to be acquired as shown in step S1 and comparison between the speeds shown in step S2 is started.

The tilting operation of the operation lever 7 causes the suspender frame 43 to tilt, and thereby the upper wire 8u is pulled.

The operation lever 7 is tilted in the up direction in the step S1, and the up/down rotation detection sensors 45A detect the tilting action of the shaft portion 7a of the operation lever 7. The up/down rotation detection sensors 45A output the detection value obtained as a result of the detection to the operation speed calculation section 61 of the control device 6. The operation speed calculation section 61 calculates the tilting operation speed (vA) of the shaft portion 7a based on the inputted detection value. The operation speed calculation section 61 outputs the calculation result to the speed determination section 62.

In the step S2, the speed determination section 62 compares the tilting operation speed (vA) of the shaft portion 7a of the operation lever 7 with the rotational speed (vP1) of the pulley 41 which is being rotated with the motor 42.

The tilting operation speed (vA) is calculated in the operation speed calculation section 61. On the other hand, the rotational speed (vP1) is determined for each voltage value at which the motor 42 is driven and registered in advance in the storage section 63.

The storage section 63 includes an assist information table, for example, and the assist information table stores the rotational speed (vP1) at the voltage V1, the rotational speed (vP2) at the voltage V2, and the rotational speed (vPn (n is equal to 1, 2, . . . ) at the voltage VN (N is equal to 1, 2, . . . ).

In the step S2, when the speed determination section 62 determines that the tilting operation speed (vA) of the operation lever 7 is slower than the rotational speed (vP1) of the pulley 41, the process moves on to the step S1. On the other hand, when the speed determination section 62 determines that the tilting operation speed (vA) of the operation lever 7 is faster than the rotational speed (vP1) of the pulley 41, the process proceeds to step S3.

When the tilting operation speed (vA) is slower than the rotational speed (vP1), the process moves on from the step S2 to the step S1 again. Then, the acquisition of the tilting operation speed of the operation lever 7 as shown in the step S1 and the comparison between the two kinds of speeds as shown in the step S2 are repeatedly performed. In this case, the motor control section 64 continues to drive the motor 42 at the voltage V1 determined in advance. As a result, the pulley 41 continues to rotate at the rotational speed (vP1).

During the continuation of the processes shown in the steps S1 and S2, the upper wire 8u is gradually brought into a pulled state from the slack state in accordance with the tilting operation of the operation lever 7. This causes the upper C-shaped ring 9u to be gradually reduced in diameter against the elastic force in accordance with the pulling of the upper wire 8u. Then, the upper C-shaped ring 9u contacts the pulley 41, to be brought into a pressed state against the pulley. The amount of tilting operation force shown by the solid line in FIG. 4A gradually increases, and also the resistance force between the upper C-shaped ring 9u and the pulley 41 gradually increases.

When the resistance force reaches a predetermined value, the upper C-shaped ring 9u rotates in the same direction as the rotation direction of the pulley 41 while sliding with respect to the pulley 41, thereby generating an assist force for pulling to move the upper wire 8u arranged on the side closer to the insertion portion 21 than the upper C-shaped ring 9u.

When the assist force for pulling the upper wire 8u is generated from the pulley 41 through the upper C-shaped ring 9u as shown in FIG. 4A, the assist force then increases as shown by the two-dot chain line in accordance with the increase in the resistance force. The amount of tilting operation force shown by the solid line is decreased in accordance with the increase in the assist force.

As a result, the operator is capable of performing the bending operation of the bending portion 25 while feeling the reduction of the amount of operation force for tilting the operation lever 7.

On the other hand, when determining that the tilting operation speed (vA) of the operation lever 7 is faster than the rotational speed (vP1) of the pulley 41 in the step S2, the speed determination section 62 outputs a notifying signal to the motor control section 64. In the step S3, the motor control section 64 which has received the notifying signal performs control for switching the rotational speed of the pulley 41 to a speed faster than the tilting operation speed (vA) of the operation lever 7 in order to prevent such a failure that the C-shaped ring 8u bites into the pulley 41 due to the high tilting operation speed. In other words, the motor control section 64 which has received the notifying signal performs control for switching the rotational speed of the pulley 41 to the speed faster than the tilting operation speed (vA) of the operation lever 7 in order to generate the assist force in accordance with the tilting operation speed of the operation lever 7.

Specifically, the motor control section 64 sets the driving voltage for driving the motor 42 to the voltage V2 (see the dashed line in FIG. 4B) higher than the initial voltage V1. The voltage V2 is a value selected by the motor control section 64 from the stored assist information table.

When the motor control section 64 sets the driving voltage of the motor 42 to the voltage V2, the rotational speed of the motor 42 increases, and the pulley 41 also rotates at the rotational speed (vP2) faster than the rotational speed (vP1).

After the change of the driving voltage, the process proceeds to step S4. The process in the step S4 is similar to that in the step S1, and the up/down rotation detection sensor 45A detects the tilting action of the shaft portion 7a to output the detection value to the operation speed calculation section 61. The operation speed calculation section 61 calculates the tilting operation speed (vA) based on the inputted detection value, to output the calculation result to the speed determination section 62.

In the step S5, the speed determination section 62 compares the tilting operation speed (vA) of the operation lever 7 with the rotational speed (vP2) of the pulley 41 rotated with the motor 42 which is driving. In this step, the tilting operation speed (vA) is a value calculated in the operation speed calculation section 61, and the rotation speed (vP2) is the rotational speed of the pulley 41 rotated with the motor 42 driven at the voltage V2.

When the speed determination section 62 determines that the tilting operation speed (vA) of the operation lever 7 is faster than the rotational speed (vP2) of the pulley 41, the process moves on to the step S3. On the other hand, when the speed determination section 62 determines that the tilting operation speed (vA) of the operation lever 7 is slower than the rotational speed (vP2) of the pulley 41, the process moves on to the step S4.

When the speed determination section 62 determines that the tilting operation speed (vA) of the operation lever 7 is slower than the rotational speed (vP2) of the pulley 41 in the step S5, the process moves on from the step S5 to step S4 again. Then, the acquisition of the tilting operation speed of the operation lever 7 as shown in the step S4 and the comparison between the two kinds of speeds as shown in the step S5 are repeatedly performed. At this time, the pulley 41 rotates at the rotational speed (vP2).

Accordingly, during the continuation of the processes shown in the steps S4 and S5, the upper wire 8u is gradually brought into a pulled state from the slack state in accordance with the tilting operation of the operation lever 7. This causes the upper C-shaped ring 9u to be gradually reduced in diameter against the elastic force in accordance with the pulling of the upper wire 8u. As a result, the upper C-shaped ring 9u contacts the pulley 41 without biting thereinto, to be brought into a pressed state against the pulley.

When the resistance force reaches a predetermined value, the upper C-shaped ring 9u generates the assist force for pulling to move the upper wire 8u as described above.

As a result, despite the tilting operation of the operation lever 7 at the high speed, the operator can perform bending operation of the bending portion 25 while feeling the reduction in the amount of operation force for tilting the operation lever 7.

That is, even though the tilting operation speed of the operation lever 7 by the operator is fast and the diameter of the upper C-shaped ring 9u is reduced by increasing the amount of tilting operation force in a short time as shown by the solid line in FIG. 4B and pulling the upper wire 8u in the slack state, a resistance force is generated between the upper C-shaped ring 9u and the pulley 41 and an assist force increases in accordance with the increase in the resistance force, thereby reducing the amount of tilting operation force as shown by the solid line. On the other hand, when determining that the tilting operation speed (vA) of the operation lever 7 is faster than the rotational speed (vP2) of the pulley 41 in the step S5, the speed determination section 62 outputs a notifying signal to the motor control section 64.

Then, the motor control section 64 performs control for switching the rotational speed of the motor 42 to a high speed again in the step S3. That is, the motor control section 64 selects the voltage value Vn corresponding to the rotational frequency faster than the tilting operation speed (vA), which is registered in the storage section 63 in advance, and controls the driving of the motor 42 again with the selected voltage value.

As a result, the rotational speed of the motor 42 increases, which causes the pulley 41 to rotate at the rotational speed (VPn) faster than the rotational speed (vP2). Then, the processes in the step S4 and step S5 are repeated.

When the bending portion 25 is brought into a bending state corresponding to the tilting operation of the operation lever 7, the tilting speed (vA) becomes "zero", and the process proceeds to step S6. The motor control section 64 changes the driving voltage of the motor 42 to the voltage V1 determined in advance, in order to restore the rotational speed of the pulley 41 to the initial state. This causes the pulley 41 to rotate at the rotational speed (vP1) which is the rotational speed in the initial state.

The tilting operation of the shaft portion 7a of the operation lever 7 is detected with the rotation detection sensor 45 to calculate the tilting operation speed (vA) of the operation lever 7 based on the detection value, and comparison is made between the calculated tilting operation speed (vA) and the rotational speed (vP1) of the pulley 41. On the basis of the comparison result, the motor control section 64 changes the voltage of the motor 42, to maintain the rotational speed of the pulley 41 or change the rotational speed of the pulley 41 to a high speed.

This surely prevents, regardless of the tilting operation speed of the operation lever 7 operated by the operator, the increase in the amount of operation force at the time of tilting operation of the operation lever 7 caused by the C-shaped rings 9u, 9d, 9l, and 9r biting into the pulley 41.

In the above-described embodiment, the tilting action of the shaft portion 7a of the operation lever 7 is detected by the rotation detection sensor to calculate the tilting operation speed, and then comparison is made between the tilting operation speed (vA) and the rotational speed (vP1) of the pulley 41. However, an acceleration sensor may be provided to detect the tilting action of the shaft portion 7a of the operation lever 7, and then comparison may be made between the tilting operation speed (vA) and the rotational speed (vP1) of the pulley 41. Alternatively, a linear sensor may be provided, for example, to detect the moving speed of the wires 8u, 8d, 8l, and 8r on the bending operation device side, instead of detecting the tilting action of the shaft portion 7a, and then comparison may be made between the tilting operation speed (vA) and the rotational speed (vP1) of the pulley 41.

In addition, the operation lever 7 that is capable of being tilted is taken as an example of the bending operation device in the above-described embodiment. However, the bending operation device is not limited to the operation lever 7, but may be a bending knob. When the bending operation device is a bending knob, the combination of the rotation detection sensor and an operation speed detection section 61 is preferable for the detection section. The rotation detection sensor detects the rotational action, which is the amount of bending operation of the shaft portion that rotates in accordance with the rotation of the bending knob, which is bending operation.

Description will be made on the second embodiment of the present invention with reference to FIGS. 6-8.

Figure 6:
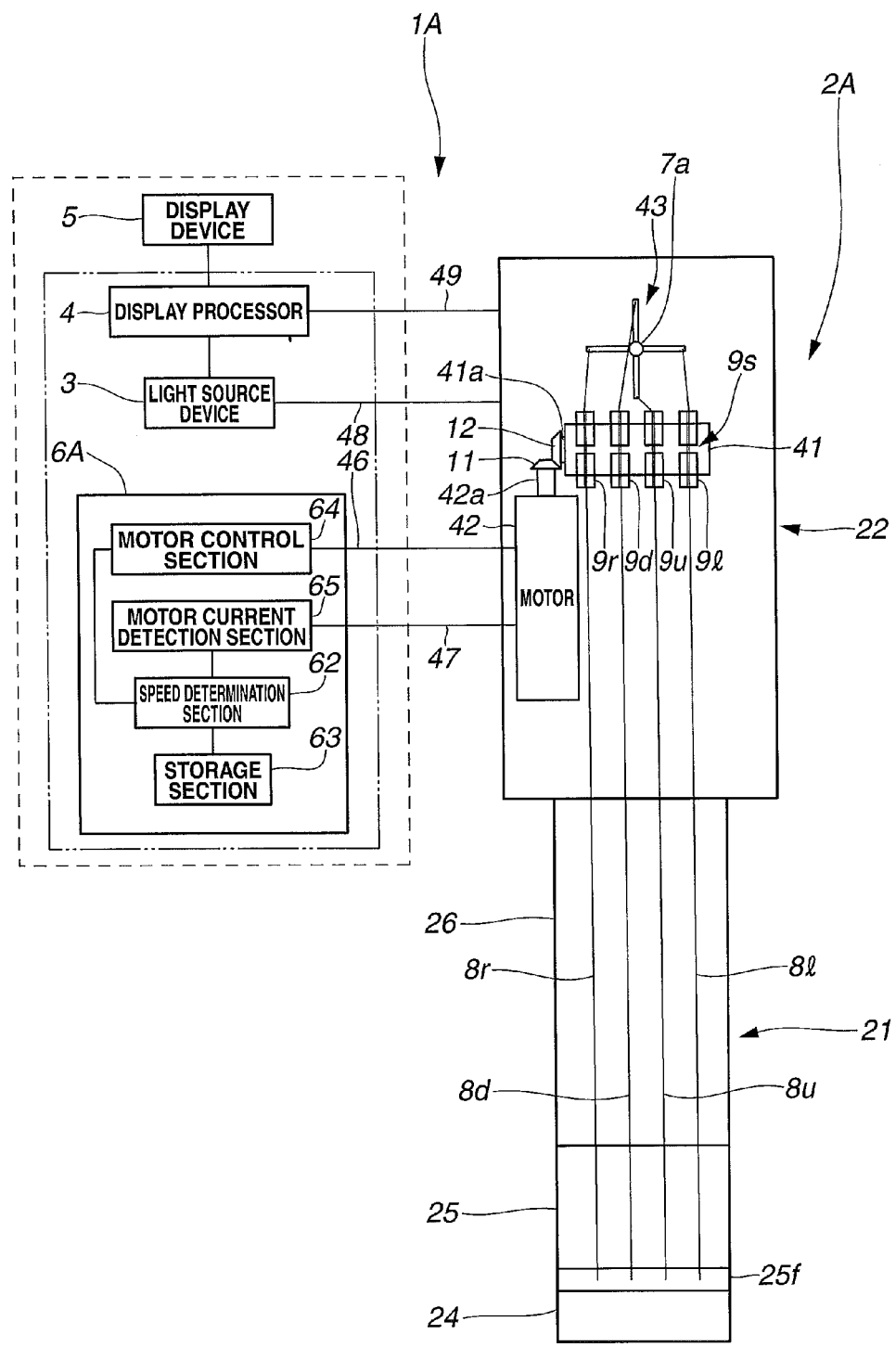

As shown in FIG. 6, an endoscope system 1A according to the present embodiment includes an endoscope 2A instead of the endoscope 2, and a control device 6A instead of the control device 6. Other configurations are the same as those in the above-described endoscope system 1. The same members are attached with the same reference signs, and description thereof will be omitted.

The endoscope 2A according to the present embodiment eliminates the need for providing the rotation detection sensors 45A, 45B that constitute the detection section provided in the operation portion 22 in the above-described endoscope 2. Other configurations of the endoscope 2A are the same as those of the endoscope 2. The same members are attached with the same reference signs and description thereof will be omitted.

The control device 6A includes a motor current increase rate detection section 65 as a detection section, instead of the above-described operation speed calculation section 61 of the control device 6. That is, the control device 6A includes the motor current increase rate detection section 65, the speed determination section 62, the storage section 63, and the motor control section 64.

During the driving of the motor 42, the motor current increase rate detection section 65 calculates an increase rate per unit time of the motor current value while constantly monitoring the current value.

The speed determination section 62 of the present embodiment compares the increase rate per unit time of the motor current calculated in the motor current increase rate detection section 65 with the motor current increase rate threshold registered in the storage section 63 in advance.

In the present embodiment, when the increase rate per unit time of the motor current is greater than the motor current increase rate threshold, the speed determination section 62 outputs a notifying signal to the motor control section 64. In addition, in the present embodiment, when the increase rate per unit time of the motor current is greater than the motor current increase rate threshold, the tilting operation speed of the operation lever 7 is determined to be faster than the rotational speed of the pulley 41.

In the present embodiment, the motor current increase rate threshold is registered in the storage section 63 in advance. The assist information table provided in the storage section 63 stores the motor current increase rate threshold corresponding to the voltage V1, the motor current increase rate threshold corresponding to the voltage V2, and the motor current increase rate threshold corresponding to the voltage VN (N is equal to 1, 2, ... ).

Other configurations of the control device 6A are the same as those of the control device 6. The same members are attached with the same reference signs and description thereof will be omitted.

Description will be made on the working of the above-described endoscope system 1A with reference to FIGS. 7A to 8.

Figure 7A:
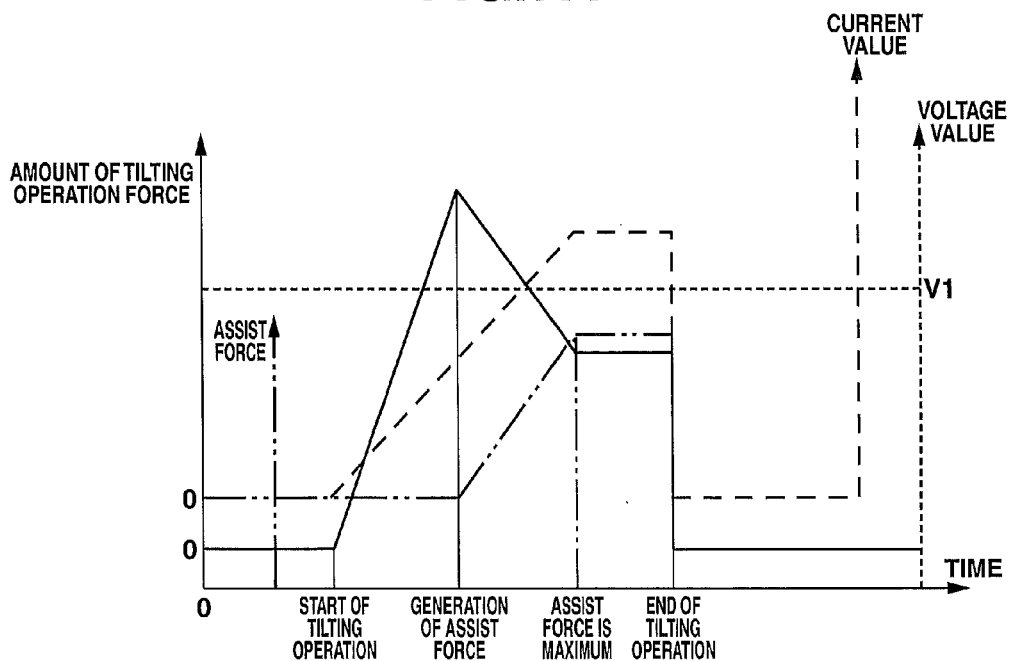
FIG. 7A illustrates a relationship among an amount of a tilting operation force, an assist force, a voltage value, and a current value from the start of the tilting operation until the end of the tilting operation in the case where the tilting operation speed is slower than the rotational speed of the pulley.
Figure 7B:
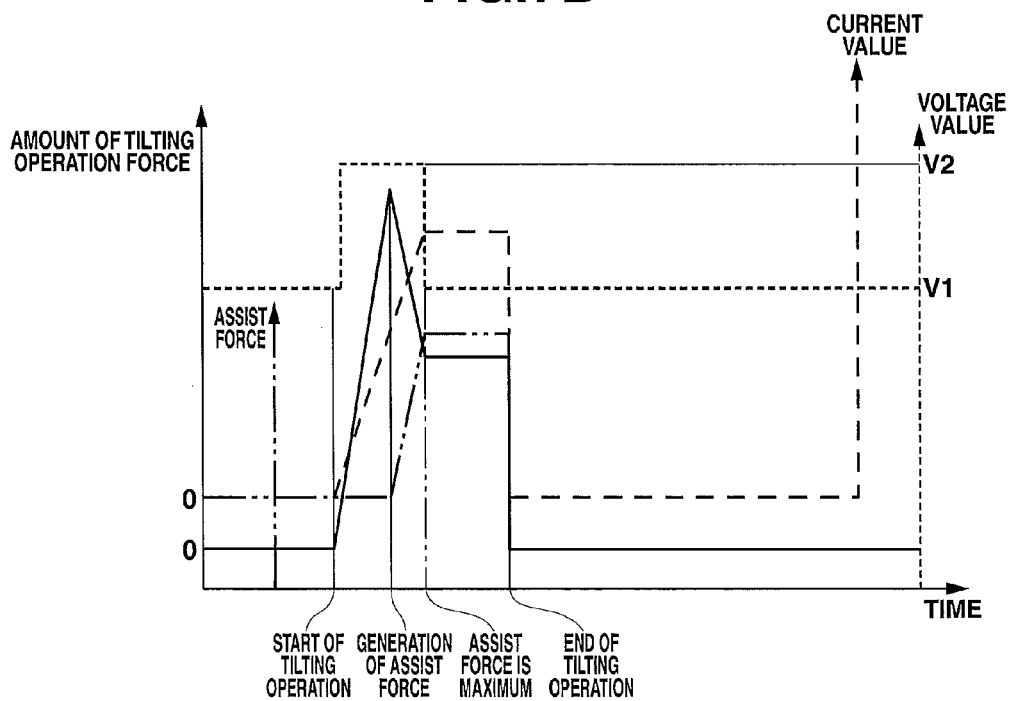
FIG. 7B illustrates a relationship among the amount of the tilting operation force, the assist force, the voltage value, and the current value from the start of the tilting operation until the end of the tilting operation.

Also in the above-described endoscope system 1A, the motor 42 provided in the endoscope 2A is driven at the voltage V1 determined in advance, as shown by the dashed lines in FIGS. 7A and 7B. In the initial state, the pulley 41 is in a state being rotated at a rotational speed (vP1) in the direction in which the wires 8u, 8d, 8l, and 8r are pulled.

When the operator performs tilting operation for allowing the bending portion 25 to bend in the up direction, for example, similarly as in the first embodiment, the tilting operation is started as shown in FIGS. 7A and 7B. The control device 6A starts the control shown in the flowchart in FIG. 8 in accordance with the start of the tilting operation.

Specifically, in the present embodiment, acquisition of the increase rate per unit time of the motor current is started in step S11, and comparison with the threshold is started as shown in step S12.

In the step S11, the motor current increase rate detection section 65 calculates the increase rate per unit time of the motor current, and outputs the acquired increase rate per unit time to the speed determination section 62. Then, in the step S12, the speed determination section 62 compares the increase rate per unit time with the motor current increase rate threshold.

When the speed determination section 62 determines that the increase rate per unit time is smaller than the motor current increase rate threshold in the step S 12, the process moves on to the step S11. On the other hand, when the speed determination section 62 determines that the increase rate per unit time is greater than the motor current increase rate threshold, the process proceeds to step S13.

When the increase rate per unit time is smaller than the motor current increase rate threshold, the process moves on from the step S12 to the step S11 again. Then, the acquisition of the increase rate per unit time of the motor current as shown in the step S11 and the comparison with the threshold as shown in the step S12 are repeatedly performed. The motor control section 64 continues to drive the motor 42 at a predetermined voltage V1. As a result, the pulley 41 continues to rotate at the rotational speed (vP1).

During the continuation of the processes in the step S11 and step S12, the upper wire 8u is gradually brought into the pulled state from the slack state in accordance with the tilting operation of the operation lever 7. As a result, similarly as in the above-described embodiment, the amount of tilting operation force gradually increases as shown by the solid line in FIG. 7A, and the resistance force between the upper C-shaped ring 9u and the pulley 41 gradually increases.

When the resistance force reaches a predetermined value, an assist force for pulling to move the upper wire 8u which is arranged on the side closer to the insertion portion 21 than the upper C-shaped ring 9u is generated similarly as in the above-described embodiment. When the assist force for pulling the upper wire 8u is generated from the pulley 41 through the upper C-shaped ring 9u as shown in FIG. 7A, the assist force then increases in accordance with the increase in the resistance force as shown by the two-dot chain line. The amount of tilting operation force shown by the solid line is decreased in accordance with the increase in the assist force.

As a result, the operator is capable of performing the bending operation of the bending portion 25 while feeling the reduction of the amount of operation force for tilting the operation lever 7, similarly as in the above-described embodiment.

On the other hand, when the increase rate per unit time is greater than the motor current increase rate threshold, the speed determination section 62 outputs a notifying signal to the motor control section 64 in the step S12.

In the step S13, the motor control section 64 which has received the notifying signal performs control for switching the rotational speed of the motor 42 to a high speed, in order to generate the assist force in accordance with the tilting operation speed of the operation lever 7.

Specifically, the motor control section 64 sets the driving voltage for driving the motor 42 to the voltage V2 (see the dashed line in FIG. 7B) higher than the initial voltage V1. The voltage V2 is a value selected by the motor control section 64 from the stored assist information table.

When the motor control section 64 sets the driving voltage of the motor 42 to the voltage V2, the rotational speed of the motor 42 increases, and the rotational speed of the pulley 41 is also changed to a high speed. That is, the pulley 41 rotates at the rotational speed (vP2) faster than the rotational speed (vP1).

After the change of the driving voltage, the process proceeds to step S14. In the step S14, the motor current increase rate detection section 65 detects the increase rate per unit time to output the detected increase rate per unit time to the speed determination section 62. In step S15, the speed determination section 62 compares the increase rate per unit time with the motor current increase rate threshold.

When the speed determination section 62 determines that the increase rate per unit time is greater than the motor current increase rate threshold, the process moves on to the step S13. On the other hand, when the speed determination section 62 determines that the increase rate per unit time is smaller than the motor current increase rate threshold, the process moves on to the step S14.

When the speed determination section 62 determines that the increase rate per unit time is smaller than the motor current increase rate threshold in the step S15, the processes in the steps S14 and S15 are repeated, thereby causing the upper C-shaped ring 9u to contact the pulley 41 without biting into the pulley 41, and then the C-shaped ring 9u is brought into a pressed state against the pulley 41.

When the resistance force reaches a predetermined value, the upper C-shaped ring 9u generates the assist force for pulling to move the upper wire 8u as described above.

As a result, despite the tilting operation of the operation lever 7 at the high speed, the operator is capable of performing the bending operation of the bending portion 25 while feeling the reduction of the amount of operation force for tilting the operation lever 7.

That is, even though the speed of the tilting operation of the operation lever 7 performed by the operator is fast and the diameter of the upper C-shaped ring 9u is reduced by increasing the amount of tilting operation force in a short time as shown by the solid line in FIG. 7B and pulling the upper wire 8u in the slack state, a resistance force is generated between the upper C-shaped ring 9u and the pulley 41 and an assist force increases in accordance with the increase in the resistance force, thereby reducing the amount of tilting operation force as shown by the solid line. On the other hand, when the speed determination section 62 determines that the increase rate per unit time is greater than the motor current increase rate threshold in the step S15, the speed determination section 62 outputs a notifying signal to the motor control section 64.

Then, the motor control section 64 performs control for switching the rotational speed of the motor 42 to a high speed again in the step S13. That is, the motor control section 64 selects the voltage value Vn from the motor current increase rate thresholds registered in advance in the storage section 63, to perform control for driving the motor 42 again at the selected voltage value.

As a result, the rotational speed of the motor 42 increases, thereby causing the pulley 41 to rotate at the rotational speed (VPn) faster than the rotational speed (vP2). After that, the processes in the step S14 and S15 are repeated.

When the bending portion 25 is brought into a bending state corresponding to the tilting operation of the operation lever 7, the increase rate per unit time becomes "zero", and the process moves on to step S16. The motor control section 64 changes the driving voltage of the motor 42 to the voltage V1 determined in advance, in order to restore the rotational speed of the motor 42 to the initial state. As a result, the pulley 41 rotates at the rotational speed (vP1) which is the rotational speed in the initial state.

Thus, in the present embodiment, the increase rate per unit time of the motor current value is acquired while constantly monitoring the motor current without providing a sensor to the endoscope, comparison is made between the increase rate per unit time and the motor current increase rate threshold, and in accordance with the comparison result, the motor control section 64 changes the voltage of the motor 42, to maintain the rotational speed of the pulley 41 or change the rotational speed to a high speed.

As a result, the same working and effects as those in the above-described embodiment can be obtained while simplifying the configuration of the endoscope.

The introducing device is not limited to an endoscope, but may be medical devices such as a forceps, a suturing instrument, an anastomosing instrument.

The present invention is not limited to the above-described embodiments and various modifications are possible without departing from the gist of argument.

What is claimed is:

1. An introducing device system comprising:
an insertion portion configured to be inserted into a subject;
a bending portion which is provided at the insertion portion and configured to be bendable;
an operation portion through which an input operation is performed for bending the bending portion;
a pulling member connected to the bending portion and pulled in accordance with the input operation through the operation portion;
a detection section configured to detect a moving speed of the pulling member that moves in accordance with the input operation;
a driving unit that rotationally drives;
a driving force transmitting unit including an inner circumferential surface configured to be able to contact an outer circumferential surface of the driving unit, and an outer circumference on which the pulling member is wound, the driving force transmitting unit being reduced in diameter in accordance with pulling of the pulling member; and
a driving unit control section configured to perform control for increasing a rotational speed of the driving unit when the moving speed detected by the detection section is higher than a speed with which the driving unit rotationally drives.

2. The introducing device system according to claim 1, wherein the detection section includes an operation speed calculation section that calculates a speed of the input operation performed through the operation portion by detecting the moving speed of the pulling member.

3. The introducing device system according to claim 1, wherein the driving force transmitting unit has a slit and is formed in a C-shape.

4. An introducing device system comprising:
an insertion portion configured to be inserted into a subject;
a bending portion which is provided at the insertion portion and configured to be bendable;
an operation portion which is operated to be tilted for bending the bending portion;
a pulling member connected to the bending portion and pulled in accordance with the tilting operation of the operation portion;
a detection section configured to detect a tilting action of the operation portion;
a driving unit that rotationally drives;
a driving force transmitting unit including an inner circumferential surface configured to be able to contact an outer circumferential surface of the driving unit, and an outer circumference on which the pulling member is wound, the driving force transmitting unit being reduced in diameter in accordance with pulling of the pulling member; and
a driving unit control section configured to perform control for increasing a rotational speed of the driving unit when a speed of the tilting action of the operation portion detected by the detection section is higher than a speed with which the driving unit rotationally drives.

5. The introducing device system according to claim 4, wherein the driving force transmitting unit has a slit and is formed in a C-shape.

* * * * *